(12) United States Patent
Kim et al.

(10) Patent No.: US 9,336,350 B2
(45) Date of Patent: May 10, 2016

(54) MEDICAL IMAGE DISPLAY APPARATUS AND METHOD

(71) Applicant: INFINITT Healthcare Co., Ltd., Seoul (KR)

(72) Inventors: Ji Min Kim, Seoul (KR); Soo Kyung Kim, Anyang-si (KR); Dae Geun Jang, Bucheon-si (KR)

(73) Assignee: INFINITT HEALTHCARE CO., LTD., Seoul (KR)

( * ) Notice: Subject to any disclaimer, the term of this patent is extended or adjusted under 35 U.S.C. 154(b) by 0 days.

(21) Appl. No.: 14/221,446

(22) Filed: Mar. 21, 2014

(65) Prior Publication Data

US 2014/0286555 A1    Sep. 25, 2014

(30) Foreign Application Priority Data

Mar. 21, 2013 (KR) .......................... 10-2013-0030162

(51) Int. Cl.
*G06K 9/00* (2006.01)
*G06F 19/00* (2011.01)

(52) U.S. Cl.
CPC .................................. *G06F 19/322* (2013.01)

(58) Field of Classification Search
CPC ........ G06F 19/322; G06T 3/40; G06T 7/0081
See application file for complete search history.

(56) References Cited

U.S. PATENT DOCUMENTS

| 8,116,544 | B2 * | 2/2012 | Masumoto | 382/128 |
| 2010/0128954 | A1 * | 5/2010 | Ostrovsky-Berman et al. | 382/131 |
| 2014/0198963 | A1 * | 7/2014 | Kim et al. | 382/128 |

FOREIGN PATENT DOCUMENTS

| KR | 10-2009-0037645 A | 4/2009 |
| KR | 10-2012-0079931 A | 7/2012 |

* cited by examiner

*Primary Examiner* — Shefali Goradia
(74) *Attorney, Agent, or Firm* — LRK Patent Law Firm

(57) ABSTRACT

A medical image display apparatus and method, which divide a screen region into a first region whose length is relatively greater than a width thereof and on which an entire lower-limb image and a division boundary line dividing the lower-limb image in a widthwise direction, and a second region adjacent to the first region, and enlarge and display a part of the lower-limb image including the division boundary line on the second region. Thereby, it is possible to minimize work for image enlargement and repetitive movement in reading a computed tomography image and to reduce the reading time.

6 Claims, 5 Drawing Sheets

MEDICAL IMAGE DISPLAY APPARATUS AND METHOD

BACKGROUND OF THE INVENTION

1. Field of the Invention

The present invention relates, in general, to a medical image display apparatus and method and, more particularly, to a medical image display apparatus and method that divide an image and enlarge and display the divided image, including a division boundary line.

2. Description of the Related Art

Computed telegraphy (CT) instruments refer to medical instruments using a CT scanner. CT instruments project X-rays or ultrasonic waves onto a human body at various angles, reconstruct the projected result using a computer, and process an internal cross section of the human body into an image. CT instruments are widely used as diagnostic instruments for tumors.

In the case of a patient whose lower limb suffers from a blood vessel disease, the CT instrument takes 1000 CT images. When the CT instrument outputs each CT image taken of the lower limb to a monitor, the CT image is displayed in a relatively snail size because the lower limb is long. A technician who processes images has to enlarge each CT image to observe blood vessels of the lower limb, and repeatedly moves between the CT images to observe each CT image individually. The image processing technician takes a long time to read and analyse the images due to the need for manual, separate image enlargement and the repeated movement between images.

SUMMARY OF THE INVENTION

Accordingly, the present invention has been made keeping in mind the above problems occurring in the related art, and the present invention is intended to propose a medical image display apparatus and method that divide an image and enlarge and display the divided image including a division boundary line.

In order to achieve the above object, according to an aspect of the present invention, a medical image display apparatus includes: an image processing unit configured to read in a lower-limb image that is a medical image obtained by performing computed tomography on lower limbs of a user and includes at least one of a bone shape and a blood vessel shape; and a display unit configured to divide the medial image and display the divided medical images on a screen region. The screen region on which the lower-limb image is displayed is divided into a first region whose length is relatively greater than a width thereof and on which the entire lower-limb image and a division boundary line dividing the lower-limb image in a widthwise direction, and a second region adjacent to the first region. The display unit enlarges and displays a part of the lower-limb image including the division boundary line on the second region. The medical image display apparatus is configured to adjust a position of the division boundary line on the first region by movement of an adjusting bar, to overlap a region outside the division boundary line to enlarge and display the lower-limb image including the outside region, to rotate the lower-limb image on the first or second region according to a rotation instruction, and to capture a two-dimensional image for the lower-limb image divided by the division boundary line while rotating based on a preset angle.

Here, the display unit may display a cross-sectional image corresponding to the lower-limb image on a third region adjacent to the second region.

According to another aspect of the present invention, a medical image display method of a medical image display apparatus that divides a lower-limb image that is a medical image having at least one of a bone shape and a blood vessel shape and displays the divided lower-limb images on a screen region includes the steps of: reading in the lower-limb image that is a medical image obtained by performing computed tomography on lower limbs of a user; dividing the screen region into a first region whose length is relatively greater than a width thereof and a second region adjacent to the first region; displaying the entire lower-limb image and a division boundary line dividing the lower-limb image in a widthwise direction on the first region; and enlarging and displaying a part of the lower-limb image including the division boundary line on the second region. The step of displaying the division boundary line includes a sub-step of adjusting a position of the division boundary line on the first region by movement of an adjusting bar, and a sub-step of rotating the lower-limb image on the first or second region according to a rotation instruction. The step of enlarging and displaying a part of the lower-limb image includes a sub-step of overlapping a region outside the division boundary line to enlarge and display the lower-limb image including the outside region, and a sub-step of capturing a two-dimensional image for the lower-limb image divided by the division boundary line while rotating based on a preset angle.

Here, the step of enlarging and displaying a part of the lower-limb image may include a sub-step of displaying a cross-sectional image corresponding to the lower-limb image on a third region adjacent to the second region.

According to the medical image display apparatus and method of the present invention, it is possible to minimise work for image enlargement and repetitive movement in reading a computed tomography image and to reduce the reading time.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
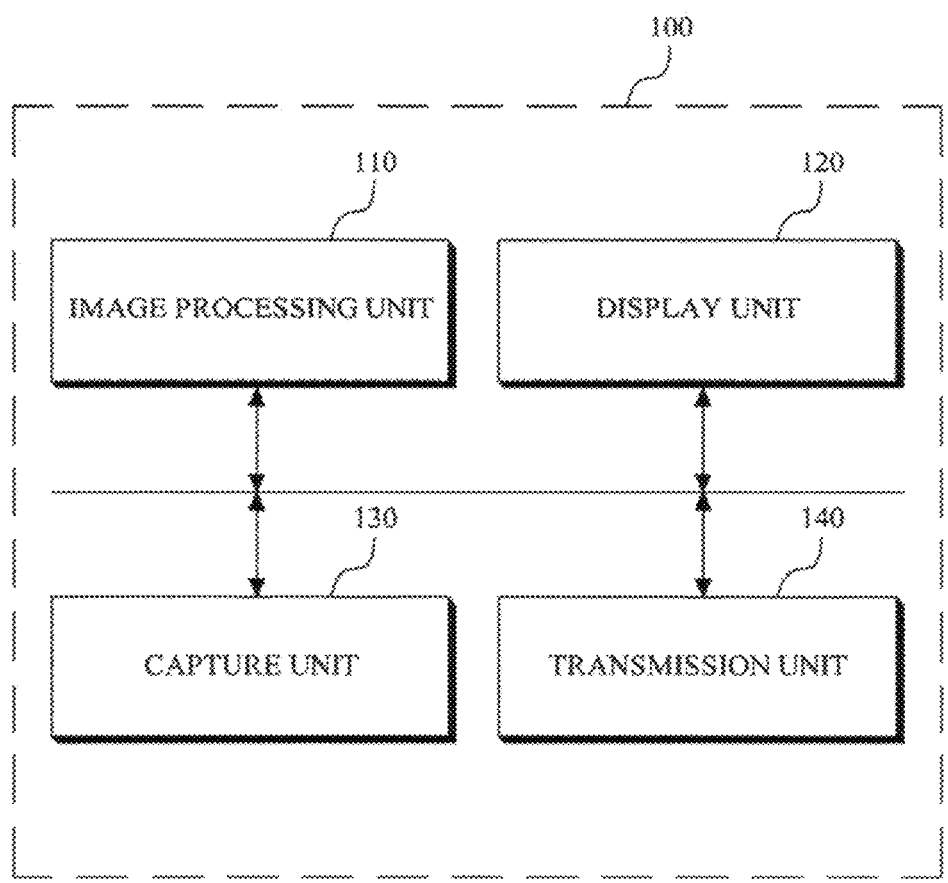
FIG. 1 is a block diagram showing a configuration of a medical image display apparatus according to an embodiment of the present invention.

The specific structural or functional description disclosed herein is merely illustrative for the purpose of describing embodiments according to the concept of the present invention. The embodiments according to the concept of the present invention can be implemented in various forms, and can not be construed as limited to the embodiments set forth herein.

The embodiments according to the concept of the present invention can be variously modified and have various shapes. Thus, the embodiments are illustrated in the drawings and are intended to be described herein in detail. However, the embodiments according to the concept of the present invention are not construed as limited to specified disclosures, and include all changes, equivalents, or substitutes that do not depart from the spirit and technical scope of the present invention.

Hereinbelow, exemplary embodiments of the present invention will be described in detail with reference to the accompanying drawings.

FIG. 1 is a block diagram showing a configuration of a medical image display apparatus according to an embodiment of the present invention.

The configuration of the medical image display apparatus will be described with reference to FIG. 1.

The medical image display apparatus 100 includes an image processing unit 110 producing an image of lower limbs, a display unit 120 that divides the lower-limb image and displays the divided lower-limb images, a capture unit 130 capturing a two-dimensional image for the lower-limb image, and a transmission unit 140 transmitting the captured two-dimensional image.

The image processing unit 110 produces the lower-limb image by removing a bone shape from the image obtained by photographing lower limbs using a computed tomography (CT) instrument. The image processing unit 110 receives the lower-limb image photographed by the CT instrument, and processes the lower-limb image into a three-dimensional image. The lower-limb image is a medical image that is photographed by the CT instrument and is processed into a two- or three-dimensional image. The image processing unit 110 provides the lower-limb image processed into the three-dimensional image to the display unit.

The display unit 120 displays the lower-limb image whose length is relatively greater than its width. The display unit 120 divides the long lower-limb image into three or four sections, and enlarges and displays the lower-limb images included in the divided sections. The display unit 120 divides the long lower-limb image in order to display a detailed image for the long lower-limb image, and enlarges and displays the lower-limb images included in the divided sections. The display unit 120 can provide image information about the lower limbs of a patient by enlarging and displaying the entire lower-limb image and the lower-limb images of the divided sections.

The display unit 110 divides and displays a screen region. The screen region includes a first region on which the long lower-limb image and a division boundary line are displayed, and a second region on which the lower-limb image including the division boundary line is enlarged and displayed. The display unit 120 divides the screen region into first and second regions, and displays the lower-limb images on the respective regions. The display unit 120 displays the long lower-limb image in whole, and enlarges and displays the lower-limb image including the division boundary line, thereby making it possible to reduce a process of enlarging the lower-limb image to move to a desired region in order to observe the lower-limb image of the desired region.

The capture unit 130 captures two-dimensional images for the lower-limb image while rotating at intervals of a preset angle. The capture unit 130 captures the two-dimensional, images for the lower-limb image divided by the division boundary line. The capture unit 130 may capture the lower-limb image according to the preset angle, and output the two-dimensional image. The preset angle refers to an angle that is preset to capture the lower-limb image by input of a user. The capture unit 130 provides the two-dimensional images captured at intervals of the preset angle to the transmission unit 140.

The transmission unit 140 transmits the captured two-dimensional images to a medical image information system according to a preset protocol. The preset protocol may be based on an image information system using a picture archiving and communication system (PACS). The medical image information system manages the captured two-dimensional images on the basis of information about a patient. The medical image information system can manage two-dimensional images having a smaller capacity than a three-dimensional lower-limb image at a minimum cost.

The medical image information system adds information about the two-dimensional image to history information, and creates updated history information. The medical image information system can reduce a time to retrieve medical images through the history information. The medical image information system can provide convenience to a client terminal that requests and receives information about a previous medical image using the history information.

The screen region of the display unit according to the first embodiment will be described below.

Figure 2:
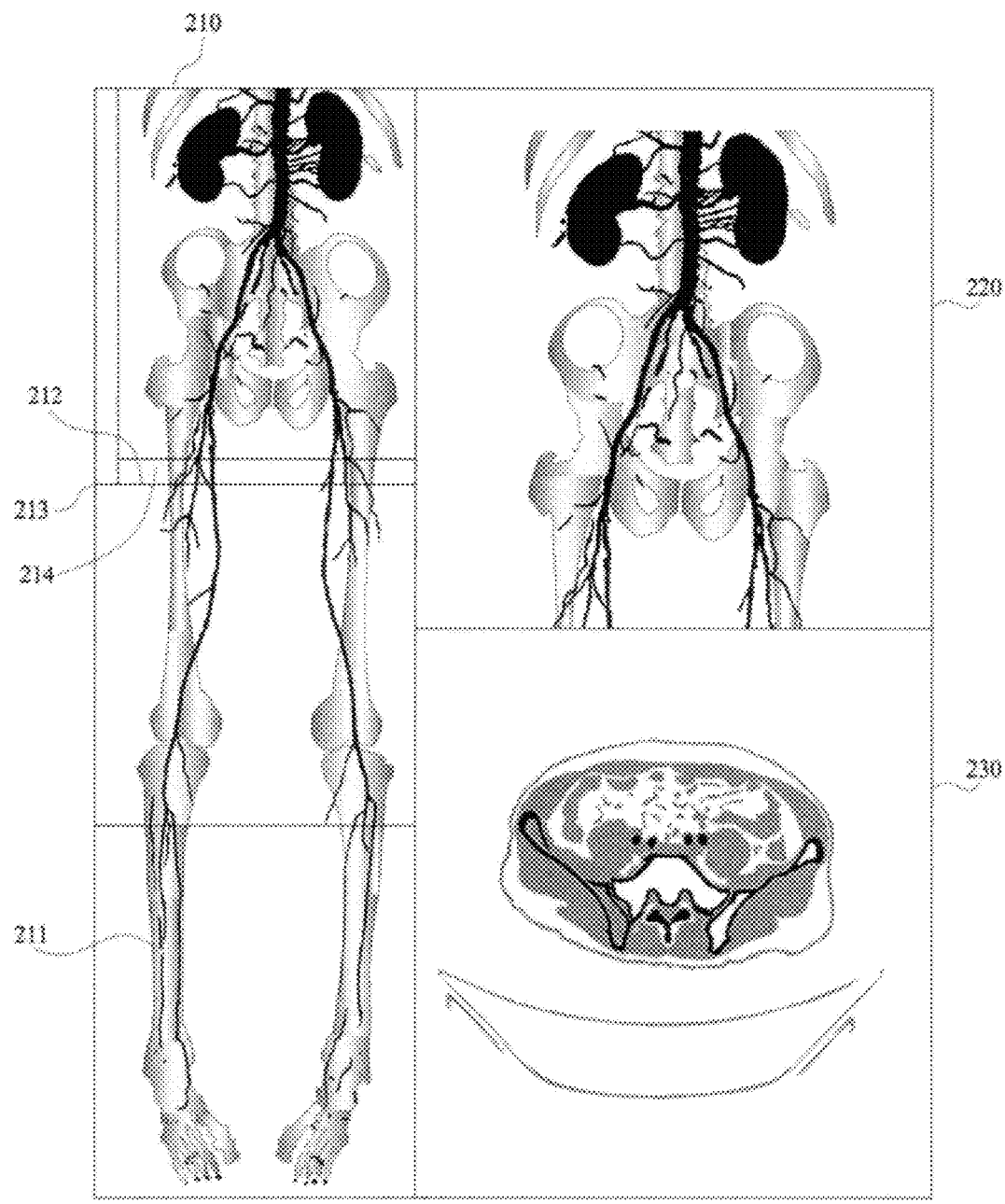
FIG. 2 illustrates a first screen configuration in accordance with the embodiment of the present invention.

FIG. 2 illustrates a first screen configuration in accordance with the embodiment of the present invention.

The first screen configuration displayed by the medical image display apparatus will be described with reference to FIG. 2.

The first screen configuration 200 includes a first region 210 on which a long lower-limb image 211 and a division boundary line 212 are displayed, a second region 220 on which a lower-limb image including the division boundary line 212 is enlarged and displayed, and a third region 230 on which a cross section or the lower-limb image is displayed. In the first screen configuration 200, the first region 210 may be disposed on the left side, and the second and third regions 220 and 230 may be disposed above and below on the right side.

The first region 210 includes an adjusting bar 213 adjusting a range of the division boundary line 212. The division boundary line 212 has an offset 214 including a region outside the boundary line. Movement of the adjusting bar 213 adjusts the region of the division boundary line 212. The offset 214 overlaps with a neighboring boundary line, and includes the region outside the boundary line.

The medical image display apparatus 100 displays the long lower-limb image 211 and the division boundary line 212 having the offset 214 on the first region 210. For example, the medical image display apparatus 100 may display the entire lower-limb image 211 and the division boundary line 212 on the first region 210. The medical image display apparatus 100 can show the entire image and the divided regions by displaying the entirety of the lower-limb image 211 and the division boundary line 212 dividing the lower-limb image 211 on the first region 210.

The lower-limb image including the division boundary line 212 on the first region 210 is enlarged and displayed on the second region 220. The division boundary line 212 includes the offset 214 overlapping with the neighboring boundary line. The second region 220 further includes the lower-limb image by the offset 214, and is displayed on a display screen.

The medical image display apparatus 100 enlarges and displays the lower-limb image including the division boundary line 212 on the second region 220. The medical image display apparatus 100 can enlarge and display the divided lower-limb image on the second region 220. The medical image display apparatus 100 can show a detailed image by enlarging and displaying the lower-limb image divided from the entire lower-limb image on the second region 220.

The third region 230 displays a cross section of the enlarged and displayed lower-limb image. The third region 230 displays the cross section of the lower-limb image, and provides information about the cross section. The medical image display apparatus 100 can display the cross section of the lower-limb image on the third region 230. In other words, the medical image display apparatus 100 can display the information about the cross section of the lower-limb image on the third region 230.

A screen region of a display unit according to a second embodiment will be described below.

Figure 3:
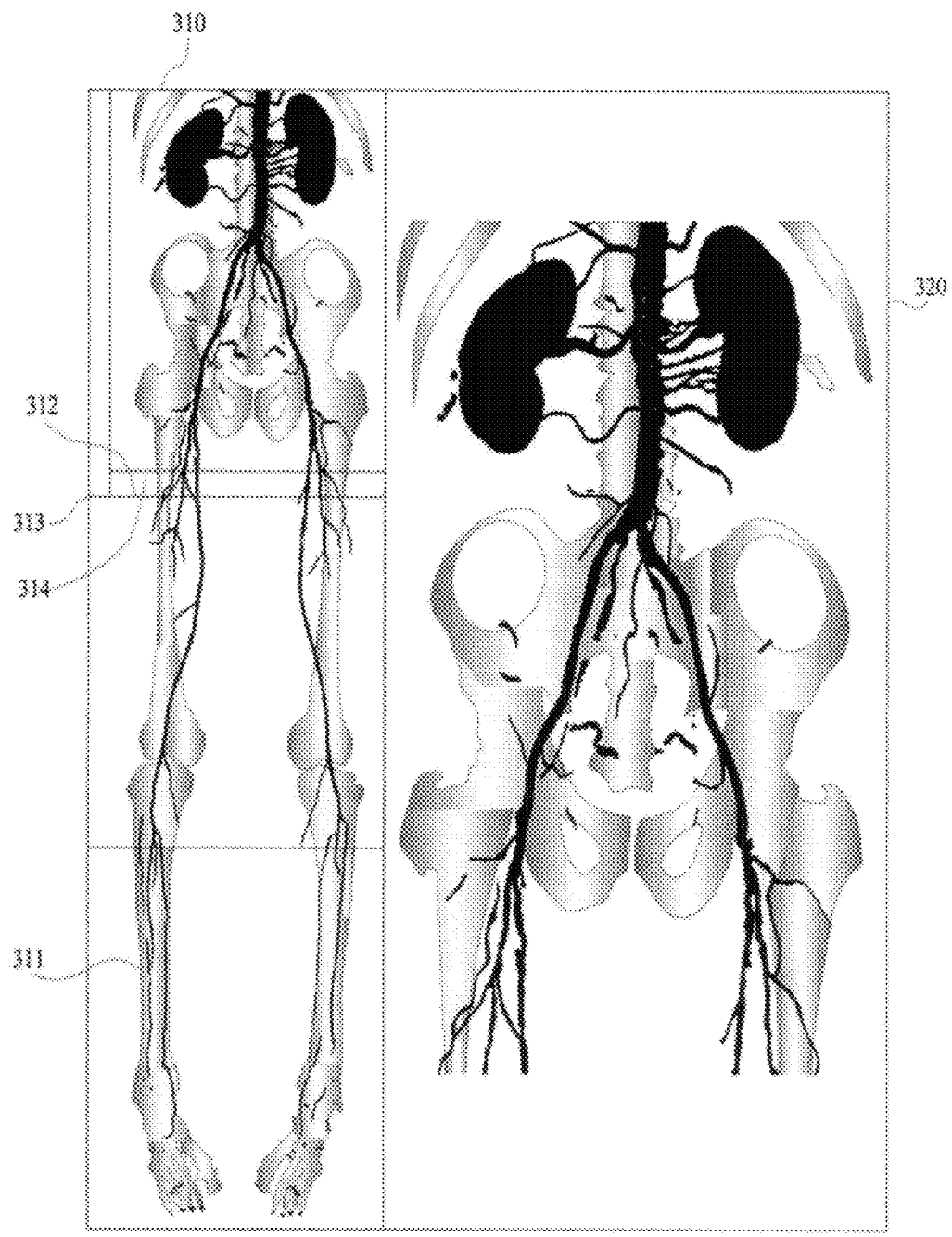
FIG. 3 illustrates a second screen configuration in accordance with the embodiment of the present invention.

FIG. 3 illustrates a second screen configuration in accordance with the embodiment at the present invention.

The second screen configuration displayed by the medical image display apparatus will be described with reference to FIG. 3.

The second screen configuration 300 includes a first region 310 on which a long lower-limb image 311 and a division boundary line 312 are displayed, and a second region 320 on which a lower-limb image including the division boundary line 312 is enlarged and displayed. In the second screen configuration 300, the first region 310 may be disposed on the left side, and the second region 320 may be disposed on the right side. A screen configuration in which the left and right sides of these regions are reversely changed is possible.

The first region 310 includes an adjusting bar 313 adjusting a range of the division boundary line 312. The division boundary line 312 has an offset 314 including a region outside the boundary line. The offset 314 may be adjusted by environment setting.

The medical image display apparatus 100 displays the long lower-limb image 311, the division boundary line 312 dividing the lower-limb image 311, and the adjusting bar 313 adjusting the range of the division boundary line 312 on the first region 310. The medical image display apparatus 100 can adjust the range of the division boundary line 312 by means of movement of the adjusting bar 313.

The lower-limb image including the division boundary line 312 on the first region 310 is enlarged and displayed on the second region 320. The second region 320 includes the region outside the boundary line by the offset 314, and displays the lower-limb image that is farther included by the offset 314.

The medical image display apparatus 100 enlarges and displays the lower-limb image including the division boundary line 312 on the second region 320. The medical image display apparatus 100 can enlarge and display the lower-limb image inside the region of the division boundary line 312 on the second region 320.

The second region 320 can rotate the lower-limb image according to a rotation instruction, and display the lower-limb image. The lower-limb image is rotated in response to the rotation instruction, and is displayed on the second region 320. The medical image display apparatus 100 can rotate the lower-limb image in response to the rotation instruction, and display the lower-limb image on the second region 320.

Figure 4:
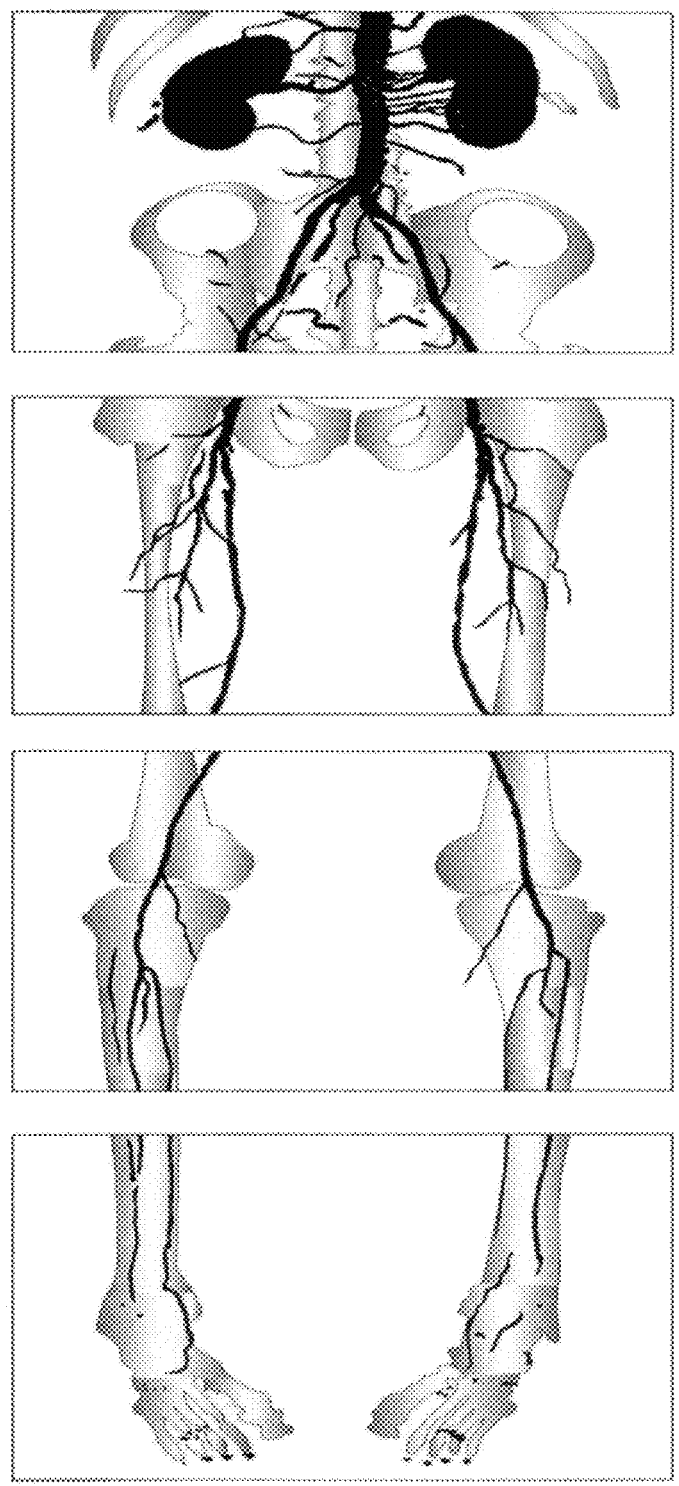
FIG. 4 is an illustrative view showing a captured image according to the embodiment of the present invention.

FIG. 4 is an illustrative view showing a captured image according to the embodiment of the present invention.

An image captured for the lower-limb image by the medical image display apparatus will be described with reference to FIG. 4.

The captured image refers to an image captured for the lower-limb image while rotating at a preset interval. The image captured for the lower-Limb image by the medical image display apparatus 100 is a two-dimensional image captured tor the lower-limb image while rotating at a preset angle.

The medical image display apparatus 100 captures an image for the rotated lower-limb image. The medical image display apparatus 100 captures an image for a three-dimensional image while rotating at a preset angle. The medical image display apparatus 100 may previously set an angle. The medical image display apparatus 100 captures the lower-limb image with reference to information about the previously set angle while rotating.

The medical image display apparatus 100 displays the captured image. The medical image display apparatus 100 may transmit the captured image to a medical image information system. The medical image information system manages the captured image so as to be kept in a database on the basis of information about a patient and enable image retrieval.

Figure 5:
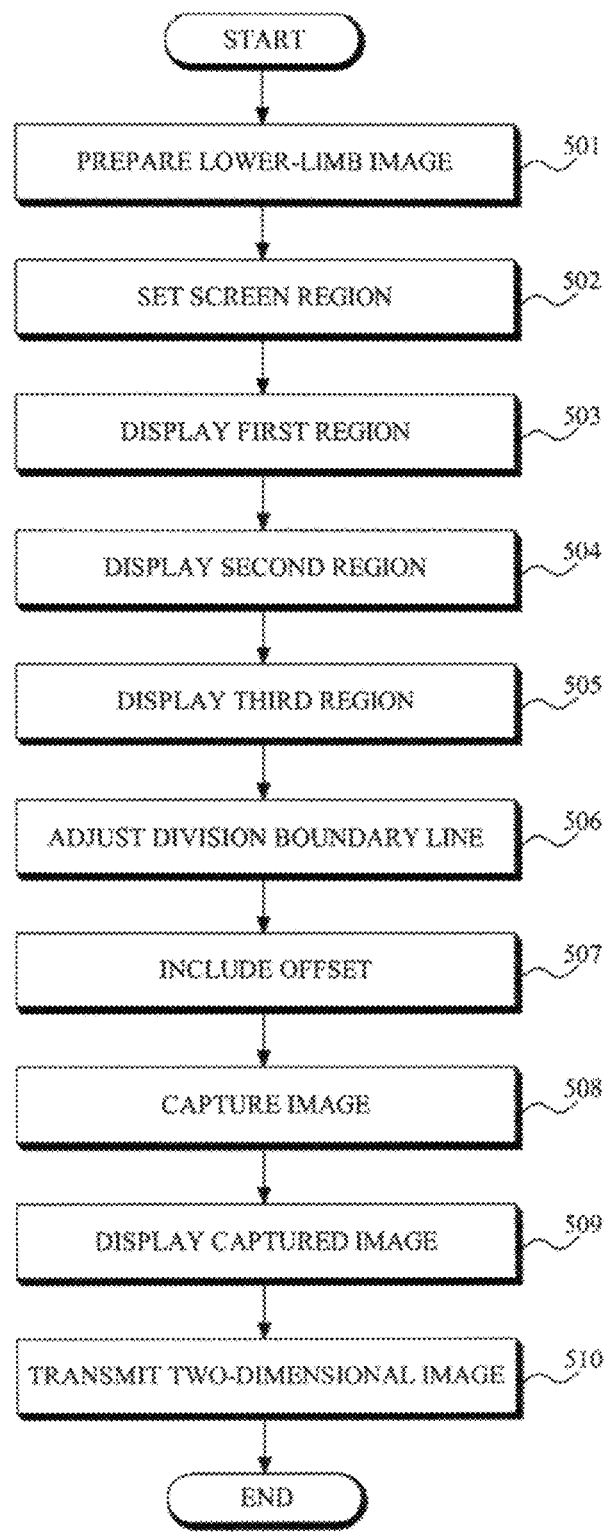
FIG. 5 is an operation flow chart showing a medical image display method according to an embodiment of the present invention.

FIG. 5 is an operation flow chart showing a medical image display method according to an embodiment of the present invention.

A method in which the medical image display apparatus displays the lower-limb image will be described with reference to FIG. 5.

The medical image display apparatus 100 prepares a lower-limb image from which a bone shape is removed and which is a long image (501). The medical image display apparatus 100 prepares the lower-limb image which is photographed by CT and from which the bone shape is removed.

The medical imago display apparatus 100 divides the long lower-limb image into three or four sections, and enlarges and displays the lower-limb images included in the divided sections. The medical image display apparatus 100 can adjust a boundary line dividing the long lower-limb image by moving the adjusting bar.

The medical image display apparatus 100 sets a first region on which the lower-limb image divided by the division boundary line is displayed, a second region on which the lower-limb image including the division boundary line is displayed, and a third section on which a cross section of the lower-limb image is displayed (502).

The medical image display apparatus 100 displays the long lower-limb image and the division boundary line on the first region (503). The medical image display apparatus 100 displays the division boundary line dividing the long lower-limb image into the preset sections.

The medical image display apparatus 100 enlarges and displays the lower-limb image including the division boundary line on the second region (504). The medical image display apparatus 100 can enlarge and display the lower-limb image, which, includes the division boundary line on the first region, on the second region.

The medical, image display apparatus 100 receives a rotation instruction, rotates the lower-limb image, and displays the lower-limb image on the first and second regions. The medical image display apparatus 100 rotates and displays the lower-limb image in response to the rotation instruction input by an operation of a mouse.

The medical image display apparatus 100 displays a cross section of the lower-limb image on the third region (505). The medical image display apparatus 100 can display the cross section of the lower-limb image, which is displayed on the second region, on the third region.

The medical image display apparatus 100 displays the adjusting bar adjusting a range of the division boundary line on the first region, adjusts the range of the division boundary line by adjusting the adjusting bar, and adjusts and displays an image display range of the second region (506).

The medical image display apparatus 100 causes an offset including a region outside the division boundary line to include the division boundary line, overlaps the offset with the image display range of the second region, and displays the overlapped result (507). The medical image display apparatus 100 displays the lower-limb image including the offset on the second region so as to be able to increase image readability.

The medical image display apparatus 100 displays the cross section of the enlarged and displayed lower-limb image on the third region. The medical image display apparatus 100 displays the cross section of the lower-limb image, and provides information about the cross section of the lower-limb image.

The medical image display apparatus 100 captures an image for the rotated lower-limb image (508). The medical image display apparatus 100 captures a two-dimensional image for the lower-limb image divided by the division boundary line. The captured image is an image captured for the lower-limb image while rotating at a preset interval.

The medical image display apparatus 100 displays the captured image (509). The medical image display apparatus 100 displays the captured image under a previous capture condition. The previous capture condition sets at which angle image capture is carried out.

The medical image display apparatus 100 transmits the captured two-dimensional image to the medical image information system (510). The medical image information system can manage the captured two-dimensional image on the basis of information about a patient.

The medical image display apparatus 100 may add the information about the two-dimensional image of the patient to history information, and create updated history information. The medical image display apparatus 100 can reduce the time required to retrieve the medical image on the basis of the history information. The medical image display apparatus 100 can provide convenience to a client terminal that requests and receives information about a previous medical image using the history information.

Although exemplary embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A medical image display apparatus comprising:
an image processing unit configured to read in a lower-limb image that is a medical image obtained by performing computed tomography on lower limbs of a user and includes at least one of a bone shape and a blood vessel shape; and
a display unit configured to divide the medical image and display the divided medical images on a screen region, wherein the screen region on which the lower-limb image is displayed is divided into a first region whose length is relatively greater than a width thereof and on which the entire lower-limb image and a division boundary line dividing the lower-limb image in a widthwise direction, and a second region adjacent to the first region,
the display unit enlarges and displays a part of the lower-limb image including the division boundary line on the second region, and
the medical image display apparatus is configured
to adjust a position of the division boundary line on the first region by movement of an adjusting bar,
to overlap a region outside the division boundary line to enlarge and display the lower-limb image including the outside region,
to rotate the lower-limb image on the first or second region according to a rotation instruction, and
to capture a two-dimensional image for the lower-limb image divided by the division boundary line while rotating based on a preset angle.

2. The medical image display apparatus according to claim 1, wherein the display unit displays a cross-sectional image corresponding to the lower-limb image on a third region adjacent to the second region.

3. A method of displaying a medical image in a medical image display apparatus for dividing a lower-limb image that is a medical image having at least one of a bone shape and a blood vessel shape and for displaying the divided lower-limb images on a screen region, the method comprising:
reading in the lower-limb image that is a medical image obtained by performing computed tomography on lower limbs of a user;
dividing the screen region into a first region whose length is relatively greater than a width thereof and a second region adjacent to the first region;
displaying the entire lower-limb image and a division boundary line dividing the lower-limb image in a widthwise direction on the first region; and
enlarging and displaying a part of the lower-limb image including the division boundary line on the second region,
wherein the displaying the division boundary line includes adjusting a position of the division boundary line on the first region by movement of an adjusting bar, and rotating the lower-limb image on the first or second region according to a rotation instruction, and
wherein the enlarging and displaying a part of the lower-limb image includes overlapping a region outside the division boundary line to enlarge and display the lower-limb image including the outside region, and capturing a two-dimensional image for the lower-limb image divided by the division boundary line while rotating based on a preset angle.

4. The method according to claim 3, wherein the enlarging and displaying a part of the lower-limb image includes displaying a cross-sectional image corresponding to the lower-limb image on a third region adjacent to the second region.

5. A non-transitory computer-readable medium intended to be read by a computer equipped with a computer program for implementing the medical image display method according to claim 3.

6. A non-transitory computer-readable medium intended to be read by a computer equipped with a computer program for implementing the medical image display method according to claim 4.

* * * * *